United States Patent [19]

Okamoto

[11] Patent Number: 5,639,824
[45] Date of Patent: Jun. 17, 1997

[54] SEPARATING AGENT CONTAINING A SUPPORT AND A CYCLODEXTRIN DERIVATIVE

[75] Inventor: Yoshio Okamoto, Aichi, Japan

[73] Assignee: Daicel Chemical Industries, Ltd., Osaka, Japan

[21] Appl. No.: 940,952

[22] PCT Filed: Feb. 28, 1992

[86] PCT No.: PCT/JP92/00232

§ 371 Date: Oct. 27, 1992

§ 102(e) Date: Oct. 27, 1992

[87] PCT Pub. No.: WO92/15617

PCT Pub. Date: Sep. 17, 1992

[30] Foreign Application Priority Data

Feb. 28, 1991 [JP] Japan .................................. 3-34048

[51] Int. Cl.$^6$ .................................................. C08F 8/00
[52] U.S. Cl. .................. 525/54.2; 525/54.3; 536/18.7; 536/103; 210/656
[58] Field of Search .......................... 210/656; 536/103, 536/18.7; 525/54.2, 54.3

[56] References Cited

U.S. PATENT DOCUMENTS

| | | | |
|---|---|---|---|
| 4,426,292 | 1/1984 | Wernick et al. | 210/635 |
| 4,539,399 | 9/1985 | Armstrong | 536/103 |
| 5,104,547 | 4/1992 | Cabrera et al. | 210/656 |
| 5,183,809 | 2/1993 | Weisz et al. | 514/58 |

FOREIGN PATENT DOCUMENTS

| | | |
|---|---|---|
| 0198395 | 10/1986 | European Pat. Off. . |
| 0445604 | 9/1991 | European Pat. Off. . |
| 0459530 | 12/1991 | European Pat. Off. . |
| 2658825 | 8/1991 | France . |
| WO90/02141 | 3/1990 | WIPO . |

OTHER PUBLICATIONS

Derwent Publications Ltd., London, GB; AN 89-042618 & JP-A-63314201, Japan Organo KK, "Fixing Cyclodextrin For Chromatographic Separate Filler Etc.", Dec. 22, 1988, Abstract (1 page).

Derwent Publications Ltd., London, GB; AN 86-321583 & JP-A-61237057, Toyo Soda Mfg. KK, "Filler For Liquid Chromatography", Oct. 22, 1986, Abstract (1 page).

File Supplier PAJ/JPO & JP-A-1053152, Tosoh Corp, "Packing Material For Liquid Chromatography", Mar. 1, 1989, Abstract (1 page).

Armstrong et al. "Derivatized Cyclodextring for Normal Phase Liquid Chromatographic Separation of Enantiomers", *Anal. Chem.* 62, 1610–1615, (Aug. 1990).

*Primary Examiner*—Jeffrey C. Mullis
*Attorney, Agent, or Firm*—Flynn, Thiel, Boutell & Tanis, P.C.

[57] ABSTRACT

Chemically bonded bodies comprising a support and a cyclic oligosaccharide derivative, at least one of the 2-, 3- and 6-position hydroxyl groups of which is chemically bonded to the support through a spacer (with the proviso that those wherein the 6-position hydroxyl group is bonded to a support through an ether linkage are excepted). A separating agent or a separating apparatus comprising such a chemically bonded body is extremely useful as a functional material for optical resolution.

12 Claims, No Drawings

SEPARATING AGENT CONTAINING A SUPPORT AND A CYCLODEXTRIN DERIVATIVE

FIELD OF INDUSTRIAL APPLICATION

The present invention relates to a chemically bonded body which comprises a cyclic oligosaccharide derivative which is extremely useful as a functional material for optical resolution, a separating agent or separating apparatus comprising said chemically bonded body, and a process for separation using said separating agent or separating apparatus.

PRIOR ART

The separating agents of the prior art comprising a polysaccharide derivative exhibit a high resolving power for various racemic modifications as a stationary phase in liquid chromatography. In the optical resolution of a racemic modification with the separating agent, it is believed to be essential that the higher-order structure of the polysaccharide derivative well fits to the structure of the racemic modification to cause effective adsorptive interaction between the polysaccharide derivative and the racemic modification. However, there are also compounds which can be difficultly resolved even by the use of a polysaccharide derivative having a high resolving power as a matter of fact.

The present inventors have made extensive studies to develop a separating agent which can resolve such difficultly resolvable compounds, with their attention being paid to cyclic oligo-saccharides which are composed of repeating units having the same structure as that of the repeating units of polysaccharide, but the number of repeating units of which is smaller than that of polysaccharide.

Although a material comprising a silane-treated silica gel and a cyclic oligosaccharide derivative physically supported thereon, beads of a cyclic oligosaccharide derivative and a material prepared by chemically bonding the 6-position hydroxyl group of a cyclic oligosaccharide to a silica gel treated with a silane treatment having a cyclic ether group at the ends and then being derivated have already been known as a stationary phase using the cyclic oligosaccharide derivative in chromatography, the resolving powers of these materials are insufficient (see U.S. Pat. No. 4,539,399 and Anal. Chem., 1990, 62, 1610).

DISCLOSURE OF THE INVENTION

For the purpose of solving the above problem, the present inventors have made extensive studies on the preparation of cyclic oligosaccharide derivatives and the resolving powers thereof and have accomplished the present invention.

Namely, the present invention provides a chemically bonded body comprising a support and a cyclic oligosaccharide derivative, at least one of the 2-, 3- and 6-position hydroxyl groups of which is chemically bonded to the support through a spacer (with the proviso that those wherein the 6-position hydroxyl group is bonded to a support through an ether linkage are excepted), a separating agent or separating apparatus comprising said chemically bonded body and a process for separation using said separating agent or separating apparatus.

The spacer includes carbamates, esters and ethers, when the 2- or 3-position hydroxyl group of the oligosaccharide derivative is chemically bonded to a support, while it includes carbamates and esters, when the 6-position hydroxyl group thereof is chemically bonded to a support.

The hydroxyl groups of the cyclic oligosaccharide derivative to be used as the raw material are classified into three groups, i.e., a group of hydroxyl groups bonded to the spacer, a group of hydroxyl groups replaced with functional groups other than the spacer, and a group of unreplaced free hydroxyl groups. Now, the hydroxyl groups not bonded to the spacer will be described.

The cyclic oligosaccharide derivative to be used in the present invention is preferably one prepared by replacing part or the whole of the hydroxyl groups of a cyclic oligosaccharide which is composed of D-glucopyranoside repeating units as represented by the following general formula (1) by functional groups having 1 to 30 carbon atoms:

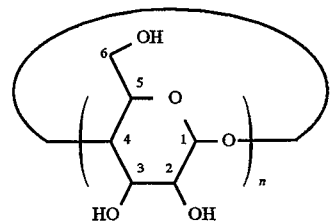

(1)

(wherein n is an integer of 5 to 13)

The present invention will now be described in detail.

CYCLIC OLIGOSACCHARIDE

The cyclic oligosaccharide to be used in the present invention is preferably an optically active compound composed of 5 to 13, preferably 6 to 8 D-glucopyranoside repeating units which are bonded to each other through α-1,4-glucosidic linkage, i.e., with a bonded form being replaced at α-position, to form a cyclic oligosaccharide. Specific examples thereof are as follows:

α-cyclodextrin (n=6),

β-cyclodextrin (n=7), and

γ-cyclodextrin (n=8).

FUNCTIONAL GROUP

The cyclic oligosaccharide derivative to be used in the present invention is preferably a cyclic oligosaccharide in which at least 70% of all the hydroxyl groups are replaced by functional groups. Although the functional group to be introduced into the cyclic oligosaccharide may be any one which is formed by the reaction with the hydroxyl group of a cyclic oligosaccharide and has 1 to 30 carbon atoms, those having an aromatic group are preferred.

Representative examples of the cyclic oligosaccharide derivative having functional groups introduced thereinto are as follows:

A) ester derivatives

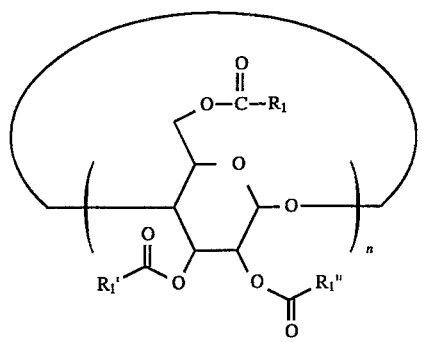

wherein $R_1$, $R_1'$ and $R_1''$ are specifically each a hydrogen atom, an alkyl group such as a methyl(—$CH_3$), ethyl (—$C_2H_5$) isopropyl, butyl, isobutyl or t-butyl group; a substituted or unsubstituted aromatic group such as a

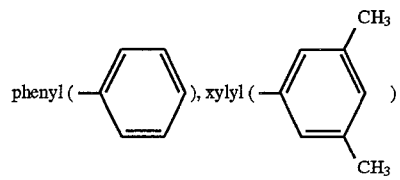

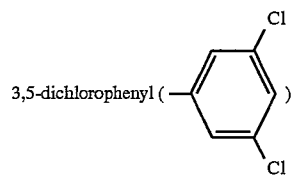

group; an aralkyl group such as a benzyl or phenethyl group, or the like. Part of the hydroxyl groups may remain without being replaced.

B) carbamate derivatives

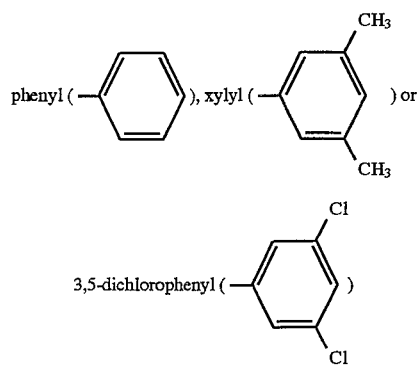

wherein $R_2$, $R_2'$ and $R_2''$ are specifically each a hydrogen atom; an alkyl group such as a methyl (—$CH_3$), ethyl (—$C_2H_5$), isopropyl, butyl, isobutyl or t-butyl group; a substituted or unsubstituted aromatic group such as a

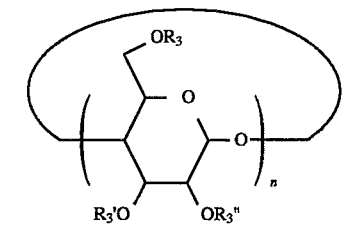

group; an aralkyl group such as a benzyl or phenethyl group, or the like. Part of the hydroxyl groups may remain without being replaced.

C) ether derivatives

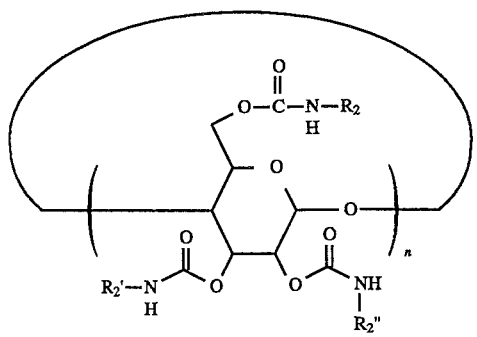

wherein $R_3$, $R_3'$ and $R_3''$ are specifically each an alkyl group such as a methyl (—$CH_3$), ethyl (—$C_2H_5$), isopropyl, butyl, isobutyl or t-butyl group, a substituted or unsubstituted aromatic group such as a

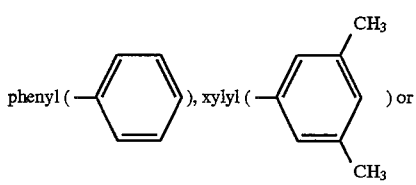

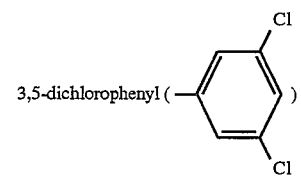

group; an aralkyl group such as a benzyl or phenethyl group, or the like. Part of the hydroxyl groups may remain without being replaced.

Further, cyclic oligosaccharide derivatives wherein the hydroxyl groups are replaced by two or more kinds of functional groups may be also used.

The degree of replacement by the functional groups is at least 70%, preferably at least 80% based on all the hydroxyl groups.

PROCESS FOR SYNTHESIS

The cyclic oligosaccharide derivatives having functional groups introduced thereinto can be prepared by the following processes:

A) ester derivatives

The ester derivative of a cyclic oligosaccharide according to the present invention can be easily prepared by reacting the corresponding carboxylic acid (RCOOH) with thionyl chloride, oxalyl chloride or the like to form an acid chloride and reacting the corresponding cyclic oligosaccharide with the acid chloride in an amount of 80 to 90% by equivalent based on all the hydroxyl groups of the cyclic oligosaccharide in pyridine as a solvent.

B) carbamate derivatives

Conventional processes for preparing a urethane from an alcohol and an isocyanate can be as such applied to the preparation of the carbamate derivatives according to the present invention. For example, the carbamate derivative can be prepared by reacting a cyclic oligosaccharide with the corresponding isocyanate (R'NCO) in an amount of 80 to 90% by equivalent based on all the hydroxyl groups of the cyclic oligosaccharide in a suitable solvent in the presence of a Lewis base such as a tertiary amine or a Lewis acid such as a tin compound as a catalyst. The isocyanate to be used can be easily prepared by reacting the amino group of the corresponding aniline derivative with phosgene.

C) ether derivatives

The ether derivative according to the present invention can be prepared by reacting the corresponding cyclic oligosaccharide with the corresponding halide R"X (wherein X represents a halogen atom) in an amount of 80 to 90% by equivalent based on all the hydroxyl groups of the cyclic oligosaccharide in dioxane or pyridine as a solvent and in the presence of a base such as potassium hydroxide or potassium t-butoxide.

Further, different kinds of functional groups can be introduced into a cyclic oligosaccharide by conducting the above processes successively.

SPACER

The spacer used in the present invention serves as a mediate compound through which at least one of the 2-, 3- and 6-position hydroxyl groups of the cyclic oligosaccharide derivative is chemically bonded to a support. The linkage through which the hydroxyl group is bonded to the support is at least one member selected from among ester, carbamate and ether linkages. The spacer includes polyfunctional compounds having at least two ester-forming functional groups, e.g., acid chloride or active ester groups, those having at least two carbamate-forming functional groups, e.g., isocyanate groups, those such as a halide and those having at least two ether-forming functional groups, e.g., OTs or OMs groups. Further, polyfunctional compounds having two or more functional groups different from each other also may be used. Polyfunctional isocyanates and polyfunctional acid halides which are representative examples of the spacer will now be described specifically.

1) polyfunctional isocyanates represented by the following formula:

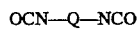

wherein Q is a residue of an aliphatic or aromatic compound having 3 to 30 atoms. Specific examples of the polyfunctional isocyanate include 4,4'-diphenylmethane diisocyanate

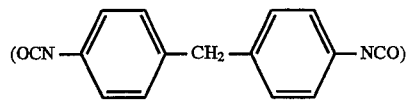

and hexamethylene diisocyanate.

2) polyfunctional acid halides represented by the following formula:

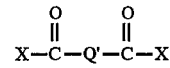

wherein Q' is a residue of an aliphatic or aromatic compound having 3 to 40 atoms and X represents a halogen, specifically Cl, Br or the like. A specific example of the polyfunctional acid halide is suberoyl chloride (ClOC—(CH$_2$)$_6$—COCl).

CHEMICALLY BONDED BODY

The above-mentioned cyclic oligosaccharide derivative according to the present invention is extremely useful as a functional material. Particularly, a chemically bonded body prepared by chemically bonding at least one of the 2-, 3- and 6-hydroxyl groups of the cyclic oligosaccharide derivative according to the present invention to a support through a carbamate, ester or ether linkage by the use of a spacer as described above (with the proviso that those wherein the 6-position hydroxyl group is bonded to a support through an ether linkage are excepted) are useful as a packing material for optical resolution, i.e., a separating agent. Among such chemically bonded bodies, one prepared by bonding at least one of the 2- and 3-position hydroxyl groups thereof to a support through a spacer is preferable. Further, one prepared by chemically bonding at least one of the 2- and 3-position hydroxyl groups of β-cyclodextrin to a support through a spacer is still preferable.

It is suitable that the separation of a compound mixture or an optical isomer mixture by the use of the chemically bonded body of the present invention as a separating agent is conducted by a chromatographic method, which uses a column packed with the chemically bonded body of the present invention, such as a gas chromatography, a liquid chromatography, a thin-layer chromatography and a supercritical chromatography.

The chemical bonding of the hydroxyl groups of the cyclic oligosaccharide to a support may be conducted by, e.g., a process which comprises reacting a cyclic oligosaccharide with an isocyanate, acid halide or halide in an amount of 80 to 90% of the stoichiometric amount to convert part or all of the highly reactive 6-position primary hydroxyl groups of the cyclic oligosaccharide and part of the lowly reactive 2- and 3-position hydroxyl groups into derivative groups and chemically bonding unreacted 2-, 3- and 6-position hydroxyl groups of the oligosaccharide to a support through a polyfunctional isocyanate, polyfunctional acid halide or polyfunctional halide.

The support to be used in the present invention may be a porous organic or inorganic support, with the use of a porous inorganic support being preferable. Suitable examples of the porous organic support include polymeric materials such as polystyrene, polyacrylamide and polyacrylate. Suitable examples of the porous inorganic support include silica, alumina, magnesia, glass, kasulion (sic), titanium oxide and silicates, which may be surface-treated for the purpose of improving the affinity thereof with the carbamate derivative and the surface characteristics of the support itself. The surface treatment includes a silane treatment with an organic silane compound and a surface treatment with plasma polymerization.

In the use of the chemically bonded body of the present invention in liquid or thin-layer chromatography as a separating agent, the developer to be used is not particularly limited except for ones which dissolve the cyclic oligosaccharide derivative or react therewith.

EXAMPLE

The present invention will now be described more specifically by referring to the following Examples, though the present invention is not limited by them.

Example 1

Preparation of a Chemically Bonded Body Comprising an Aminopropylsilane-treated Silica Gel and 3,5-dimethyl-phenylcarbamate Derivative of β-cyclodextrin Bonded Thereto Through 4,4'-diphenylmethane Diisocyanate as a Spacer (1) Preparation of aminopropylsilane-treated silica gel 20 g of vacuum-dried silica gel (Develosil 100-5, a product of Nomura Kagaku) was dispersed in a mixture comprising dry benzene (250 ml) and dry pyridine (2 ml), followed by the addition of 3-aminopropyltriethoxysilane (5 ml). The obtained mixture was heated under reflux for 15 hours under a nitrogen stream and poured Into excess tetrahydrofuran. The resulting mixture was filtered through a G4 glass filter. The silane-treated silica gel thus recovered was washed with methanol, acetone and hexane to give the objective substance.

The results of the elemental analysis of the silane-treated silica gel thus obtained are given in Table 1.

TABLE 1

| Elemental analysis | | $NH_2$ group on the surface of silica | No. of reacted |
|---|---|---|---|
| % C | % N | (μmmol/m$^2$) | OH groups/nm$^2$ |
| 5.27 | 1.16 | 2.7 | 2.6 |

(2) Preparation of a chemically bonded body comprising the silica gel and 3,5-dimethylphenylcarbamate derivative of β-cyclodextrin bonded thereto through a spacer (4,4'-diphenylmethane diisocyanate)

1.22 g (8.31 mmol, 90% by equivalent based on all the hydroxyl groups of the starting material) of 3,5-dimethylphenyl isocyanate was added to a solution of 0.5 g (0.44 mmol) of β-cyclodextrin (a product of Nacarai Kagaku) in 12 ml of anhydrous pyridine. The obtained mixture was heated at 80° C. in a nitrogen stream for 3 hours. The disappearance of the absorption (2200 to 2300 cm$^{-1}$) assignable to the isocyanate (—N═C═O) group of the starting material and the appearance of the absorption (1700 cm$^{-1}$) assignable to the carbonyl (C═O) group of the objective compound were ascertained by FT-IR spectroscopy, followed by the addition of 0.6 g (1.84 mmol, twice as much as the residual hydroxyl groups) of 4,4'-diphenylmethane diisocyanate. The obtained mixture was further stirred under heating for 3 hours and distilled under a reduced pressure to remove the solvent. The residue was washed with n-hexane thrice. The β-cyclodextrin derivative thus obtained was dissolved in a solvent mixture comprising tetrahydrofuran (10 ml) and pyridine (2 ml), followed by the addition of 3 g of the silane-treated silica gel prepared in the above step (1). The obtained mixture was maintained at 80° C. for 15 hours to conduct a reaction. The reaction mixture was poured into tetrahydrofuran and the resulting mixture was filtered through a G4 glass filter. The filter cake was washed with tetrahydrofuran, pyridine, methanol and hexane and vacuum dried at 60° C. for 5 hours to give the objective substance.

Example 2

Preparation of a Chemically Bonded Body Comprising an Aminopropylsilane-treated Silica Gel and 3,5-dimethylphenylcarbamate Derivative of β-cyclodextrin Bonded Thereto Through Hexamethylene Diisocyanate as a Spacer 1.22 g (8.31 mmol, 90% by equivalent based on all the hydroxyl groups of the starting material) of 3,5-dimethylphenyl isocyanate was added to a solution of 0.5 g (0.44 mmol) of β-cyclodextrin (a product of Nacarai Kagaku) in 12 ml of anhydrous pyridine. The obtained mixture was heated at 80° C. in a nitrogen stream for 3 hours. The disappearance of the absorption (2200 to 2300 cm$^{-1}$) assignable to the isocyanate (—N═C═O) group of the starting material and the appearance of the absorption (1700 cm$^{-1}$) assignable to the carbonyl (C═O) group of the objective compound were ascertained by FT-IR spectroscopy, followed by the addition of 0.3 g (1.84 mmol, twice as much as the residual hydroxyl groups) of hexamethylene diisocyanate. The obtained mixture was further stirred under heating for 3 hours and distilled under a reduced pressure to remove the solvent. The residue was washed thrice with n-hexane. The β-cyclodextrin derivative thus obtained was dissolved in a solvent mixture comprising 10 ml of tetrahydrofuran and 2 ml of pyridine, followed by the addition of 3 g of the silane-treated silica gel prepared in the step (1) of Example 1. The obtained mixture was maintained at 80° C. for 15 hours to conduct a reaction and the reaction mixture was poured into tetrahydrofuran. The precipitates were collected by filtering the resulting mixture through a G4 glass filter and the precipitates were washed with tetrahydrofuran, pyridine, methanol and hexane, and vacuum dried at 60° C. for 5 hours to give the objective substance.

Example 3

Preparation of a Chemically Bonded Body Comprising an Aminopropylsilane-treated Silica Gel and 3,5-dimethylphenylcarbamate Derivative of β-cyclodextrin Bonded Thereto Through Suberoyl Chloride as a Spacer 1.22 g (8.31 mmol, 90% by equivalent based on all the hydroxyl groups of the starting material) of 3,5-dimethylphenyl isocyanate was added to a solution of 0.5 g (0.44 mmol) of β-cyclodextrin (a product of Nacarai Kagaku) in a solvent mixture comprising 10 ml of anhydrous tetrahydrofuran and 2 ml of anhydrous pyridine. The obtained mixture was heated at 80° C. in a nitrogen stream for 3 hours. The disappearance of the absorption (2200 to 2300 cm$^{-1}$) assignable to the isocyanate (—N═C═O) group of the starting material and the appearance of the absorption (1700 cm$^{-1}$) assignable to the carbonyl (C═O) group of the objective compound were ascertained by FT-IR spectroscopy, followed by the addition of 0.39 g (1.84 mmol, twice as much as the residual hydroxyl groups) of suberoyl chloride. The obtained mixture was further stirred under heating for 3 hours and distilled under a reduced pressure to remove the solvent. The residue was washed thrice with n-hexane. The β-cyclodextrin derivative thus prepared was dissolved in a solvent mixture comprising 10 ml of tetrahydrofuran and 2 ml of pyridine, followed by the addition of 3.0 g of the silane-treated silica gel prepared in the step (1) of Example 1. The obtained mixture was maintained at 80° C. for 15 hours to conduct a reaction. The resulting reaction mixture was poured into tetrahydrofuran and the precipitates were collected by filtering the obtained mixture through a G4 glass filter. The precipitates were washed with tetrahydrofuran, pyridine, methanol and hexane, and vacuum dried at 60° C. for 5 hours to give the objective substance.

The results of analysis of the chemically bonded bodies prepared in Examples 1 to 3 are given in Table 2.

TABLE 2

|  | Ex. 1 | Ex. 2 | Ex. 3 |
|---|---|---|---|
| No. of spacers per molecule of β-cyclodextrin derivative | 1 | 2 | 1~2 |
| Content of β-cyclodextrin derivative in chemically bonded body (% by wt.) | 11 | 17 | 13 |
| Molar amount of β-cyclodextrin derivative per surface area of chemically bonded body (μmol/m$^2$) | 0.10 | 0.17 | 0.12 |

Example 4

The chemically bonded bodies prepared in Examples 1 to 3 as separating agents were each packed in a stainless steel column having an inner diameter of 0.46 cm and a length of 25 cm by the slurry method.

Various racemic modifications listed in Table 3 were each resolved by the use of these columns under the following conditions and the results are given in Table 3.

CONDITIONS OF RESOLUTION composition of mobile phase: in the case of the racemic modifications 1 to 10, n-hexane/2-propanol=90/10 (v/v), while in the case of the racemic modification 11, n-hexane/2-propanol=70/30 (v/v)

flow rate: 0.5 ml/min.

The capacity ratio (k') and separation factor (α) given in the Tables were calculated by the following formulas, respectively, and in the Tables, Ph represents a phenyl group and Me a methyl group.

$$\text{capacity ratio } (k') = \frac{\text{retention time of separated compound} - \text{dead time}}{\text{dead time}}$$

$$\text{separation factor } (\alpha) = \frac{\text{capacity ratio of more strongly adsorbed compound}}{\text{capacity ratio of more weakly adsorbed compound}}$$

TABLE 3

| Racemic modification |  | Ex. 1 k'(±) | Ex. 1 α | Ex. 2 k'(±) | Ex. 2 α | Ex. 3 k'(±) | Ex. 3 α |
|---|---|---|---|---|---|---|---|
| 1 | (epoxide with Ph, Ph) | 0.72(+) | 1.16 | 0.63(+) | 1.16 | 0.85(−) | ~1 |
| 2 | (epoxide with CNHPh, PhNHC) | 2.31(+) | 1.44 | 2.94 | 1.45 | 3.17(+) | 1.42 |
| 3 | Tröger's base | 0.99(−) | 1.15 | — | — | 1.10(−) | 1.09 |
| 4 | (cyclohexanone with Ph) | 1.35(−) | 1.10 | 1.68(−) | 1.05 | 1.42(−) | 1.09 |
| 5 | (binaphthol-Me,Me with OH,OH) | — | — | — | — | 5.39(−) | 1.05 |
| 6 | benzoin | 3.98(+) | 1.03 | 1.65 | 1.0 | 3.95(+) | 1.03 |
| 7 | flavanone | 2.24(+) | 1.98 | 2.22(+) | 1.27 | 2.19(+) | 1.69 |

TABLE 3-continued

| Racemic modification | Ex. 1 k'(±) | Ex. 1 α | Ex. 2 k'(±) | Ex. 2 α | Ex. 3 k'(±) | Ex. 3 α |
|---|---|---|---|---|---|---|
| 8 (Ph)₃C—CH(Ph)—OH | 1.95(−) | 1.12 | 1.45 | 1.0 | 1.79(−) | 1.09 |
| 9 binaphthol | — | | 11.8 | 1.07 | 12.7(−) | 1.02 |
| 10 (structure) | 6.57(−) | 1.08 | 7.30(−) | 1.03 | 6.79(−) | 1.13 |
| 11 (structure) | 8.84(−) | 1.40 | — | | 9.95(−) | 1.35 |

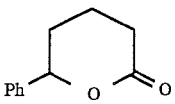

Example 5

Preparation of a Chemically Bonded Body Wherein the 6-Position Hydroxyl Group of 3,5-dimethylphenylcarbamate Derivative of β-cyclodextrin is Chemically Bonded to an Aminopropyl-treated Silica Gel Through 4,4'-diphenylmethane Diisocyanate as a Spacer The silane-treated silica gel (3.0 g) prepared in the step (1) of Example 1 was dispersed in a mixture comprising tetrahydrofuran (10 ml) and pyridine (1 ml), followed by the addition of 4,4'-diphenylmethane diisocyanate (24 mg, 0.09 mmol). The obtained mixture was maintained at 80° C. for 3 hours to conduct a reaction, followed by the addition of 1.3 equivalents (136 mg, 0.12 mmol) of β-cyclodextrin, N,N-dimethylacetamide (10 ml) and pyridine (1 ml). The obtained mixture was maintained at 80° C. for 3 hours to conduct a reaction, followed by the addition of 3,5-dimethylphenyl isocyanate (714 mg, 4.36 mmol). The mixture thus obtained was reacted at that temperature for 15 hours and poured into tetrahydrofuran. The precipitates were collected by filtering the resulting mixture through a G4 glass filter and the precipitates were washed with tetrahydrofuran, pyridine, methanol and hexane and vacuum dried at 60° C. for 5 hours to give the objective substance.

Example 6

Preparation of a Chemically Bonded Body Wherein the β-position Hydroxyl Group of 3,5-dimethylphenylcarbamate Derivative of β-cyclodextrin is Chemically Bonded to an Aminopropyl-treated Silica Gel Through Hexamethylene Diisocyanate as a Spacer The same procedure as that of Example 5 was repeated except that hexamethylene diisocyanate (15 mg, 0.09 mmol) was used as a spacer instead of the 4,4'-diphenylmethane diisocyanate, thus giving the objective substance.

Example 7

Preparation of a Chemically Bonded Body Wherein the β-position Hydroxyl Group of 3,5-dimethylphenylcarbamate Derivative of β-cyclodextrin is Chemically Bonded to an Aminopropyl-treated Silica Gel Through Suberoyl Chloride as a Spacer The same procedure as that of Example 5 was repeated except that suberoyl chloride (19 mg, 0.09 mmol) was used as a spacer instead of the 4,4'-diphenylmethane diisocyanate thereby giving the objective substance.

Example 8

The chemically bonded bodies prepared in Examples 5 to 7 as separating agents were each packed in a stainless steel column having an inner diameter of 0.46 cm and a length of 25 cm by the slurry method.

Various racemic modifications listed in Table 4 were each resolved by the use of these columns under the following conditions and the results are given in Table 4.

CONDITIONS OF RESOLUTION composition of mobile phase:

in the case of the racemic modifications 1 to 10, n-hexane/2-propanol=90/10 (v/v), while in the case of the racemic modification 11, n-hexane/2-propanol=70/30 (v/v)

flow rate: 0.5 ml/min.

TABLE 4

| Racemic modification | | Ex. 5 | | Ex. 6 | | Ex. 7 | |
|---|---|---|---|---|---|---|---|
| | | k'(±) | α | k'(±) | α | k'(±) | α |
| 1 | (cyclopropane with O-Ph and Ph substituents) | 0.28 | ~1 | 0.31 | ~1 | 0.29(+) | ~1 |
| 2 | (cyclopropane with PhNHC(O)- and -C(O)NHPh) | 0.69(+) | 1.20 | 0.64(+) | 1.17 | 0.86(+) | 1.23 |
| 3 | Tröger's base | 0.57 | 1.0 | 0.62(−) | ~1 | 0.55(−) | ~1 |
| 4 | 2-phenylcyclohexanone | 0.71(−) | ~1 | 0.72(−) | ~1 | 0.74(−) | ~1 |
| 5 | 2,2'-dihydroxy-3,3'-dimethyl-1,1'-biphenyl | 0.94 | 1.0 | 1.10 | 1.0 | 1.54 | 1.0 |
| 6 | benzoin | 1.41 | 1.0 | 1.45(+) | 1.05 | 1.50(+) | 1.07 |
| 7 | flavanone | 0.71(+) | ~1 | 0.79(+) | ~1 | 0.75(+) | 1.13 |
| 8 | (Ph)₃C—CH(Ph)—OH | 0.56 | 1.0 | 0.60 | 1.0 | 0.66 | 1.0 |
| 9 | binaphthol | 1.99(+) | 1.05 | 2.40(+) | ~1 | 3.15(+) | ~1 |
| 10 | (δ-lactone with Ph substituent) | 2.39(+) | ~1 | 2.86(+) | ~1 | 2.78(+) | ~1 |
| 11 | 3,5-dinitro-N-(1-phenylethyl)benzamide | — | | 4.40(−) | 1.09 | 4.35(−) | 1.12 |

Example 9

A mixture prepared by blending 3.0 g of silica gel (Develosil 100-5, a product of Nomura Kagaku) surface treated with 3-aminopropyltriethoxysilane with 16.3 mg (0.06 mmol, 50% based on the amino group of the silica gel) of 4,4'-diphenylmethane diisocyanate (a product of Tokyo Kasei) was heated at 80° C. in dry toluene for about 24 hours. Separately, 0.18 g (0.14 mmol) of β-cyclodextrin (a product of Nacarai Tesque) was dissolved in about 5 ml of dry dimethyl sulfoxide (DMSO), followed by the addition of 2.0 g (0.008 mmol) of 4,4'-diphenylmethane diisocyanate. The resulting mixture was added to the above reaction vessel containing the treated silica gel. The contents of the vessel were maintained at 80° C. by heating for 24 hours, followed by the addition of 0.49 g (3.33 mmol) of 3,5-dimethylphenyl isocyanate. The resulting mixture was further maintained at 80° C. by heating for 24 hours and poured into tetrahydrofuran (THF). The precipitates were collected by filtering the obtained mixture through a 4G glass filter and the precipitates were fully washed with THF and vacuum dried at 60° C. for 2 hours to give an objective substance.

yield: 3.30 g, elemental analysis: C: 16.58%, H: 2.19%, N: 2.45%.

Example 10

0.3 g (0.23 mmol) of γ-cyclodextrin and 0.78 g (5.31 mmol, 90% based on the hydroxyl groups) of 3,5-dimethylphenyl isocyanate were stirred together in dry pyridine under heating at 80° C. for 5 hours, followed by the addition of 0.30 g (1.20 mmol, twice as much as the residual hydroxyl groups) of 4,4'-diphenylmethane diisocyanate. The obtained mixture was further stirred under heating for 3 hours and poured into dry benzene. The obtained mixture was centrifuged to collect precipitates. The recovered precipitates were washed with dry benzene four times to wash away excess 4,4'-diphenylmethane diisocyanate. The γ-cyclodextrin carbamate derivative thus prepared was dissolved in about 20 ml of dry pyridine and the obtained solution was added to 3.0 g of Develosil 100-5 surface treated with 3-aminopropyltriethoxysilane. The obtained mixture was maintained at 80° C. for about 24 hours to conduct a reaction. The reaction mixture was poured into THF and the precipitates were collected by filtering the obtained mixture through a G4 glass filter. The precipitates were fully washed with THF and vacuum dried at 60° C. for 2 hours to give an objective substance.

yield: 3.32 g, elemental analysis: C: 17.73%, H: 1.95%, N: 2.71%.

Example 11

0.3 g (0.23 mmol) of Δ-cyclodextrin and 0.78 g (5.31 mmol, 90% based on the hydroxyl groups) of 3,5-dimethylphenyl isocyanate were stirred together under heating at about 80° C. in dry pyridine for 5 hours, followed by the addition of 0.07 g (0.60 mmol) of 3-isocyanatopropyltriethoxysilane (a product of Lancaster Synthesis Ltd.). The obtained mixture was further stirred under heating for 5 hours. After the disappearance of the absorption assignable to the isocyanate group had been ascertained by IR spectroscopy, 0.10 g (0.68 mmol) of 3,5-dimethylphenyl isocyanate was added to the resulting mixture. The reaction was continued for an additional two hours and the reaction system was evacuated to distill away the solvent and excess isocyanate. The γ-cyclodextrin derivative thus prepared was dissolved in dry pyridine and the obtained solution was added to 3.0 g of non-surface-treated Develosil 100-5. The obtained mixture was maintained at 80° C. for about 24 hours to conduct a reaction, followed by the addition of 2.0 g (18.4 mmol) of trimethylchlorosilane (a product of Shin-Etsu Chemical Co. Ltd.). The obtained mixture was reacted for an additional 24 hours and poured into THF. The precipitates were collected by filtering the resulting mixture through a 4G glass filter. The precipitates were fully washed with THF and vacuum dried at 60° C. for 2 hours to give an objective substance.

yield: 3.44 g.

Example 12

0.3 g (0.23 mmol) of γ-cyclodextrin and 0.10 g (0.41 mmol, 9% based on the hydroxyl groups) of 3-isocyanatopropyltriethoxysilane were stirred together under heating at about 80° C. in dry pyridine for 5 hours, followed by the addition of 0.92 g (6.85 mmol) of 3,5-dimethylphenyl isocyanate. The obtained mixture was stirred under heating for additional 5 hours and the reaction system was evacuated to distill away the solvent. The γ-cyclodextrin derivative thus obtained was dissolved in about 20 ml of dry pyridine and the obtained solution was added to 3.0 g of non-surface-treated Develosil 100-5. The obtained mixture was reacted at 80° C. for about 24 hours, followed by the addition of 2.0 g (18.4 mmol) of trimethylchlorosilane. The reaction was continued for additional 24 hours. The reaction mixture was poured into THF and the precipitates were collected by filtering the resulting mixture through a 4G glass filter. The filter cake was fully washed with THF and vacuum dried at 60° C. for 2 hours to give an objective substance.

yield: 3.31 g.

Example 13

The separating agents prepared in Examples 9 to 12 were each packed in a stainless steel column having an inner diameter of 0.46 cm and a length of 25 cm by the slurry method using methanol.

Various racemic modifications listed in Tables 5 and 6 were each resolved by the use of these columns and the results are given in Tables 5 and 6.

TABLE 5

| Racemic modification | Ex. 9 | | Ex. 10 | | Ex. 11 | | Ex. 12 | |
|---|---|---|---|---|---|---|---|---|
| | k' | α | k' | α | k' | α | k' | α |
| 1. $C_6H_5$–C(O)–$C_6H_5$ type structure | 0.66 | 1.08 | 0.60(−) | ~1 | 0.33(−) | ~1 | 0.30(+) | ~1 |
| 2. N-containing fused ring structure | 1.47 | ~1 | 1.33(−) | ~1 | 0.57(−) | ~1 | 0.38(+) | ~1 |
| 3. biphenyl with OH OH and $CH_3$ $CH_3$ | 1.84 | 1.08 | 1.60(−) | ~1 | 1.19(−) | ~1 | 0.67(+) | ~1 |
| 4. Ph–CH(OH)–C(O)–Ph | 4.87 | 1.05 | 1.87(−) | 1.08 | 1.25(−) | ~1 | 0.80 | 1.00 |

TABLE 5-continued

| Racemic modification | Ex. 9 | | Ex. 10 | | Ex. 11 | | Ex. 12 | |
|---|---|---|---|---|---|---|---|---|
| | k' | α | k' | α | k' | α | k' | α |
| 5. 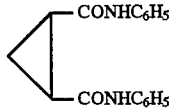 | 1.87 | 1.25 | 1.93(+) | 1.15 | 1.00(−) | ~1 | 0.93(+) | ~1 | note) eluent: n-hexane/2-propanol (90/10), flow rate: 0.5 ml/min.

TABLE 6

| Racemic modification | Ex. 9 | | Ex. 10 | | Ex. 11 | | Ex. 12 | |
|---|---|---|---|---|---|---|---|---|
| | k' | α | k' | α | k' | α | k' | α |
| 6. (chromanone with $C_6H_5$) | 2.13 | 1.18 | 1.30 | 1.00 | 0.73(+) | ~1 | 0.40(+) | ~1 |
| 7. (2-phenylcyclohexanone) | 1.55 | ~1 | ~0.7 | ~1 | 1.87(−) | ~1 | 0.43 | 1.00 |
| 8. $(C_6H_5)_3C-CH(C_6H_5)-OH$ | 1.67 | ~1 | 0.90 | 1.00 | 0.57(+) | ~1 | 0.33(+) | ~1 |
| 9. (9-anthryl-CH(CF_3)-OH) | 2.45 | ~1 | 1.37 | 1.00 | 1.06 | 1.00 | 0.38(+) | ~1 |
| 10. Co(acac)$_3$ | 0.67 | ~1 | 0.40(−) | ~1 | 1.27(−) | ~1 | 0.33(−) | ~1 | note) eluent: n-hexane/2-propanol (90/10), flow rate: 0.5 ml/min.

I claim:

1. A chemically bonded body comprising a support and a cyclodextrin derivative having a 2-position hydroxyl group, 3-position hydroxyl group and 6-position hydroxyl group, said cyclodextrin derivative having 3,5-dimethylphenylcarbamate at one of said 2-position hydroxyl group, 3-position hydroxyl group and 6-position hydroxyl group and being bonded to said support through a spacer at another of said 2-position hydroxyl group or 3-position hydroxyl group, said spacer containing a member selected from the group consisting of a carbamate group and an ester group and not containing an ether group.

2. A separating agent or a separating apparatus comprising the chemically bonded body as set forth in claim 1.

3. In a process for resolving a racemic modification into optical isomers, the improvement comprising contacting the racemic modification with the separating agent or separating apparatus as set forth in claim 2 to resolve said racemic modification.

4. A chemically bonded body as set forth in claim 1, wherein the cyclodextrin is selected from the group consisting of α-cyclodextrin, β-cyclodextrin and γ-cyclodextrin.

5. A chemically bonded body as set forth in claim 1, wherein the 3,5-dimethylphenylcarbamate is bonded at the 2-position hydroxyl group or 3-position hydroxyl group.

6. A chemically bonded body as set forth in claim 1, wherein said spacer contains a substituted or unsubstituted phenyl group.

7. A chemically bonded body as set forth in claim 1, wherein said support is aminopropyl-treated silica gel and said cyclodextrin derivative is a 3,5-dimethylphenylcarbamate derivative of β-cyclodextrin.

8. A chemically bonded body as set forth in claim 1, wherein said spacer is formed from 4,4'-diphenylmethane diisocyanate.

9. A chemically bonded body as set forth in claim 1, wherein said spacer is formed from hexamethylene diisocyanate.

10. A chemically bonded body as set forth in claim 1, wherein said spacer is formed from suberoyl chloride.

11. A chemically bonded body as set forth in claim 1, wherein said cyclodextrin derivative is a cyclodextrin compound comprising D-glucopyranoside repeating units as represented by the following general formula (1)

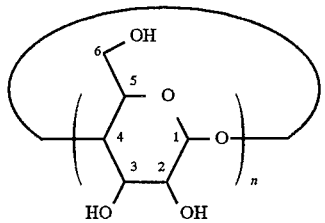

(1)

wherein n is an integer of 5 to 13.

12. A chemically bonded body comprising a support and a cyclodextrin derivative having a 2-position hydroxyl group, 3-position hydroxyl group and 6-position hydroxyl group, said cyclodextrin derivative having 3,5-dimethylphenylcarbamate at one of said 2-position hydroxyl group, 3-position hydroxyl group and 6-position hydroxyl group and being bonded to said support through a spacer at another of said 2-position hydroxyl group or 3-position hydroxyl group, said spacer being selected from among 4,4'-diphenylmethane diisocyanate, hexamethylene diisocyanate and suberoyl chloride.

* * * * *